US009536189B2

United States Patent
Rao

(10) Patent No.: US 9,536,189 B2
(45) Date of Patent: Jan. 3, 2017

(54) PHASE-CODING FOR COORDINATE TRANSFORMATION

(71) Applicant: QUALCOMM Incorporated, San Diego, CA (US)

(72) Inventor: Naveen Gandham Rao, San Diego, CA (US)

(73) Assignee: QUALCOMM INCORPORATED, San Diego, CA (US)

( * ) Notice: Subject to any disclaimer, the term of this patent is extended or adjusted under 35 U.S.C. 154(b) by 261 days.

(21) Appl. No.: 14/226,696

(22) Filed: Mar. 26, 2014

(65) Prior Publication Data

US 2015/0235124 A1 Aug. 20, 2015

Related U.S. Application Data

(60) Provisional application No. 61/942,557, filed on Feb. 20, 2014.

(51) Int. Cl.
| | | |
|---|---|---|
| G06E 1/00 | (2006.01) | |
| G06E 3/00 | (2006.01) | |
| G06F 15/18 | (2006.01) | |
| G06G 7/00 | (2006.01) | |
| G06N 3/04 | (2006.01) | |
| G06F 19/00 | (2011.01) | |
| G06F 17/17 | (2006.01) | |
| G06F 11/08 | (2006.01) | |

(52) U.S. Cl.
CPC .............. *G06N 3/049* (2013.01); *G06F 11/08* (2013.01); *G06F 17/17* (2013.01); *G06F 19/345* (2013.01); *G06N 3/04* (2013.01)

(58) Field of Classification Search
None
See application file for complete search history.

(56) References Cited

U.S. PATENT DOCUMENTS

2013/0204819 A1 8/2013 Hunzinger et al.
2013/0297541 A1 11/2013 Piekniewski et al.

FOREIGN PATENT DOCUMENTS

WO 2005017825 A2 2/2005

OTHER PUBLICATIONS

Models of Grid Cell Spatial Firing Published 2005-2011-2012 EricA.Zilli*Eric A. Zilli Department of Psychology,Center for Memory and Brain, Boston University, Boston, MA, USA.*
Putting Egocentric and Allocentric into Perspective—2010 Tobias Meilinger1 and Gottfried Vosgerau2.*
Learning Mechanisms in Networks of Spiking Neurons—2006 QingXiang Wu12, Martin McGinnity1, Liam Maguire1, Brendan Glackin1, Ammar Belatreche1.*
Neuron phase shift adaptive to time delay in locomotor control—2007 Kunishige Ohgane a,*, Shin-Ichiro Ei b, Hitoshi Maharac.*
(Continued)

*Primary Examiner* — Wilbert L Starks
*Assistant Examiner* — Ababacar Seck
(74) *Attorney, Agent, or Firm* — Seyfarth Shaw LLP

(57) ABSTRACT

A method for coordinate transformation in a spiking neural network includes encoding a first positional representation as phase information in the spiking neural network. The method also includes shifting the phase information to modify the first positional representation into a second positional representation.

18 Claims, 15 Drawing Sheets

(56) References Cited

OTHER PUBLICATIONS

Giocomo L., et al., "Computational Models of Grid Cells", Neuron, vol. 71, No. 4, Aug. 25, 2011 (Aug. 25, 2011), pp. 589-603, XP028271996, ISSN: 0896-6273, DOI: 10.1016/J.NEURON.2011. 07.023 [retrieved on Jul. 29, 2011] p. 589-p. 600, right-hand column, paragraph 2.

Hartley T., et al., "Space in the brain: how the hippocampal formation supports spatial cognition", Journal of Experimental Medicine, vol. 297, No. 5868, Dec. 23, 2013 (Dec. 23, 2013), pp. 1-18, XP055184662, ISSN: 1476-4687, DOI: 10.1038/297681a0 p. 1-p. 13, right-hand column, paragraph 4.

International Search Report and Written Opinion—PCT/US2015/015695—ISA/EPO—Apr. 30, 2015.

Touretzky D.S., et al., "Neural Representation of Space in Rats and Robots", Computational Intelligence: Imitating Life, Proceedings of the symposium held at the 1994 IEEE World Congress on Computational Intelligence, Jan. 1, 1994 (Jan. 1, 1994), pp. 57-68, XP055184626, Retrieved from the Internet: URL: http://www.ri.cmu.edu/pub_files_pub2/touretzky_dave_1994_2/touretzky_dave_1994_2.pdf [retrieved on Apr. 21, 2015] p. 1-p. 10, paragraph 4.

Touretzky D.S., et al., "Neural Representation of Space Using Sinusoidal Arrays", Neural Computation, Massachusetts Institute of Technology, US, vol. 5, No. 6, Nov. 1, 1993 (Nov. 1, 1993), pp. 869-884, XP008058867, ISSN: 0899-7667 p. 869-p. 882, paragraph 4.

Wu Q., et al., "Adaptive Co-ordinate Transformation Based on a Spike Timing-Dependent Plasticity Learning Paradigm", Jul. 23, 2005 (Jul. 23, 2005), Advances in Natural Computation; [Lecture Notes in Computer Science; LNCS], Springer-Verlag, Berlin/Heidelberg, pp. 420-428, XP019014013, ISBN: 978-3-540-28323-2 p. 420-p. 426.

Zhang L., et al., "Configurable Neural Phase Shifter With Spike-Timing-Dependent Plasticity", IEEE Electron Device Letters, IEEE Service Center, New York, NY, US, vol. 31, No. 7, Jul. 1, 2010 (Jul. 1, 2010), pp. 716-718, XP011310646, ISSN: 0741-3106 p. 716-p. 718, right-hand column, paragraph 2.

Floreano D., et al., "Evolution of spiking neural controllers for autonomous vision-based robots," Gomi T., Ed., Springer-Verlag, 2001, pp. 38-61.

Mudra R., "A Robot using a Modular Navigation System : Attentional Manoeuvring based on an Egocentric Spatial Representation," Diss. ETH No. 14681 nat. sc. SFIT Zurich, 2002, 273 Pages.

Wang X., et al., "A behavior controller based on spiking neural networks for mobile robots," Neurocomputing, 2008, vol. 71 (4-6), pp. 655-666.

\* cited by examiner

PHASE-CODING FOR COORDINATE TRANSFORMATION

CROSS-REFERENCE TO RELATED APPLICATION

This application claims the benefit under 35 U.S.C. §119(e) to U.S. Provisional Patent Application No. 61/942,557 entitled "Phase-coding for coordinate transformation," filed on Feb. 20, 2014, the disclosure of which is expressly incorporated by reference herein in its entirety.

BACKGROUND

Field

Certain aspects of the present disclosure generally relate to neural system engineering and, more particularly, to systems and methods phase-coding neural spikes to transform coordinates.

Background

An artificial neural network, which may comprise an interconnected group of artificial neurons (i.e., neuron models), is a computational device or represents a method to be performed by a computational device. Artificial neural networks may have corresponding structure and/or function in biological neural networks. However, artificial neural networks may provide innovative and useful computational techniques for certain applications in which traditional computational techniques are cumbersome, impractical, or inadequate. Because artificial neural networks can infer a function from observations, such networks are particularly useful in applications where the complexity of the task or data makes the design of the function by conventional techniques burdensome. Thus, it is desirable to provide a neuromorphic receiver to transform coordinates represented by the spike phase of target cells by adjusting the phase-coding of neural spikes.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

SUMMARY

In one aspect of the present disclosure, a method for coordinate transformation in a spiking neural network is presented. The method includes encoding a first positional representation as phase information in the spiking neural network. The method also includes shifting the phase information to modify the first positional representation into a second positional representation.

Another aspect of the present disclosure is directed to an apparatus including means for encoding a first positional representation as phase information in the spiking neural network. The apparatus also includes means for shifting the phase information to modify the first positional representation into a second positional representation.

In another aspect of the present disclosure, a computer program product for a spiking neural network having a non-transitory computer-readable medium is disclosed. The computer readable medium has non-transitory program code recorded thereon which, when executed by the processor(s), causes the processor(s) to perform operations of encoding a first positional representation as phase information in the spiking neural network. The program code also causes the processor(s) to shift the phase information to modify the first positional representation into a second positional representation.

Another aspect of the present disclosure is directed to a spiking neural network having a memory and at least one processor coupled to the memory. The processor(s) is configured to encode a first positional representation as phase information in the spiking neural network. The processor(s) is also configured to shift the phase information to modify the first positional representation into a second positional representation.

Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Based on the teachings, one skilled in the art should appreciate that the scope of the disclosure is intended to cover any aspect of the disclosure, whether implemented independently of or combined with any other aspect of the disclosure. For example, an apparatus may be implemented or a method may be practiced using any number of the aspects set forth. In addition, the scope of the disclosure is intended to cover such an apparatus or method practiced using other structure, functionality, or structure and functionality in addition to or other than the various aspects of the disclosure set forth. It should be understood that any aspect of the disclosure disclosed may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses or objectives. Rather, aspects of the disclosure are intended to be broadly applicable to different technologies, system configurations, networks and protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

An Example Neural System, Training and Operation

Figure 1:
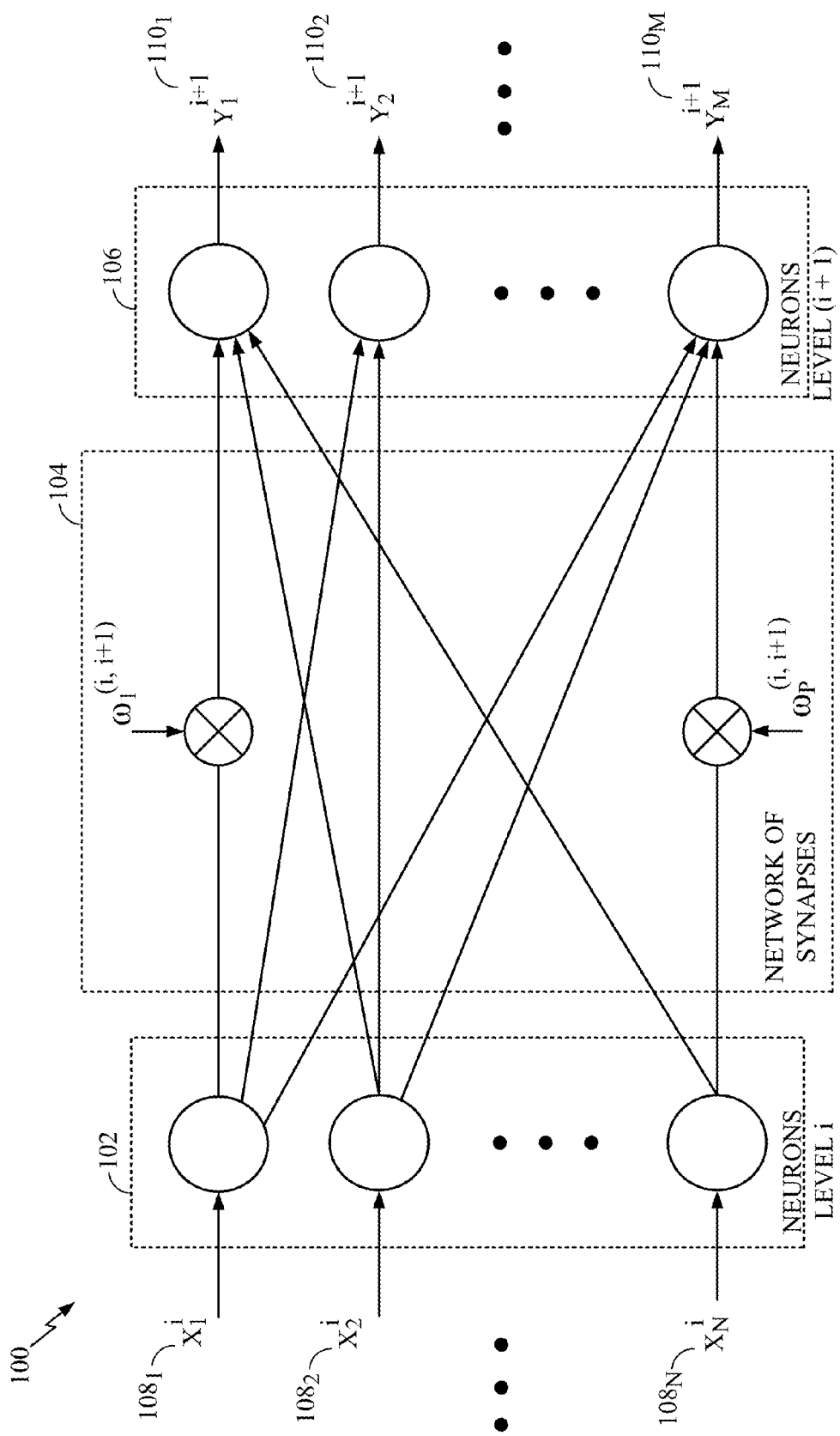
FIG. 1 illustrates an example network of neurons in accordance with certain aspects of the present disclosure.

FIG. 1 illustrates an example artificial neural system 100 with multiple levels of neurons in accordance with certain aspects of the present disclosure. The neural system 100 may have a level of neurons 102 connected to another level of neurons 106 through a network of synaptic connections 104 (i.e., feed-forward connections). For simplicity, only two levels of neurons are illustrated in FIG. 1, although fewer or more levels of neurons may exist in a neural system. It should be noted that some of the neurons may connect to other neurons of the same layer through lateral connections. Furthermore, some of the neurons may connect back to a neuron of a previous layer through feedback connections.

As illustrated in FIG. 1, each neuron in the level 102 may receive an input signal 108 that may be generated by neurons of a previous level (not shown in FIG. 1). The signal 108 may represent an input current of the level 102 neuron. This current may be accumulated on the neuron membrane to charge a membrane potential. When the membrane potential reaches its threshold value, the neuron may fire and generate an output spike to be transferred to the next level of neurons (e.g., the level 106). In some modeling approaches, the neuron may continuously transfer a signal to the next level of neurons. This signal is typically a function of the membrane potential. Such behavior can be emulated or simulated in hardware and/or software, including analog and digital implementations such as those described below.

In biological neurons, the output spike generated when a neuron fires is referred to as an action potential. This electrical signal is a relatively rapid, transient, nerve impulse, having an amplitude of roughly 100 mV and a duration of about 1 ms. In a particular embodiment of a neural system having a series of connected neurons (e.g., the transfer of spikes from one level of neurons to another in FIG. 1), every action potential has basically the same amplitude and duration, and thus, the information in the signal may be represented only by the frequency and number of spikes, or the time of spikes, rather than by the amplitude. The information carried by an action potential may be determined by the spike, the neuron that spiked, and the time of the spike relative to other spike or spikes. The importance of the spike may be determined by a weight applied to a connection between neurons, as explained below.

The transfer of spikes from one level of neurons to another may be achieved through the network of synaptic connections (or simply "synapses") 104, as illustrated in FIG. 1. Relative to the synapses 104, neurons of level 102 may be considered presynaptic neurons and neurons of level 106 may be considered postsynaptic neurons. The synapses 104 may receive output signals (i.e., spikes) from the level 102 neurons and scale those signals according to adjustable synaptic weights $w_1^{(i,i+1)}, \ldots, w_P^{(i,i+1)}$ where P is a total number of synaptic connections between the neurons of levels 102 and 106 and i is an indicator of the neuron level. In the example of FIG. 1, i represents neuron level 102 and i+1 represents neuron level 106. Further, the scaled signals may be combined as an input signal of each neuron in the level 106. Every neuron in the level 106 may generate output spikes 110 based on the corresponding combined input signal. The output spikes 110 may be transferred to another level of neurons using another network of synaptic connections (not shown in FIG. 1).

Biological synapses can mediate either excitatory or inhibitory (hyperpolarizing) actions in postsynaptic neurons and can also serve to amplify neuronal signals. Excitatory signals depolarize the membrane potential (i.e., increase the membrane potential with respect to the resting potential). If enough excitatory signals are received within a certain time period to depolarize the membrane potential above a threshold, an action potential occurs in the postsynaptic neuron. In contrast, inhibitory signals generally hyperpolarize (i.e., lower) the membrane potential. Inhibitory signals, if strong enough, can counteract the sum of excitatory signals and prevent the membrane potential from reaching a threshold. In addition to counteracting synaptic excitation, synaptic inhibition can exert powerful control over spontaneously active neurons. A spontaneously active neuron refers to a neuron that spikes without further input, for example due to its dynamics or a feedback. By suppressing the spontaneous generation of action potentials in these neurons, synaptic inhibition can shape the pattern of firing in a neuron, which is generally referred to as sculpturing. The various synapses 104 may act as any combination of excitatory or inhibitory synapses, depending on the behavior desired.

The neural system 100 may be emulated by a general purpose processor, a digital signal processor (DSP), an application specific integrated circuit (ASIC), a field programmable gate array (FPGA) or other programmable logic device (PLD), discrete gate or transistor logic, discrete hardware components, a software module executed by a processor, or any combination thereof. The neural system 100 may be utilized in a large range of applications, such as image and pattern recognition, machine learning, motor control, and alike. Each neuron in the neural system 100 may be implemented as a neuron circuit. The neuron membrane charged to the threshold value initiating the output spike may be implemented, for example, as a capacitor that integrates an electrical current flowing through it.

In an aspect, the capacitor may be eliminated as the electrical current integrating device of the neuron circuit, and a smaller memristor element may be used in its place. This approach may be applied in neuron circuits, as well as in various other applications where bulky capacitors are utilized as electrical current integrators. In addition, each of the synapses 104 may be implemented based on a memristor element, where synaptic weight changes may relate to changes of the memristor resistance. With nanometer feature-sized memristors, the area of a neuron circuit and synapses may be substantially reduced, which may make implementation of a large-scale neural system hardware implementation more practical.

Functionality of a neural processor that emulates the neural system 100 may depend on weights of synaptic connections, which may control strengths of connections between neurons. The synaptic weights may be stored in a non-volatile memory in order to preserve functionality of the processor after being powered down. In an aspect, the synaptic weight memory may be implemented on a separate external chip from the main neural processor chip. The synaptic weight memory may be packaged separately from the neural processor chip as a replaceable memory card. This may provide diverse functionalities to the neural processor, where a particular functionality may be based on synaptic weights stored in a memory card currently attached to the neural processor.

Figure 2:
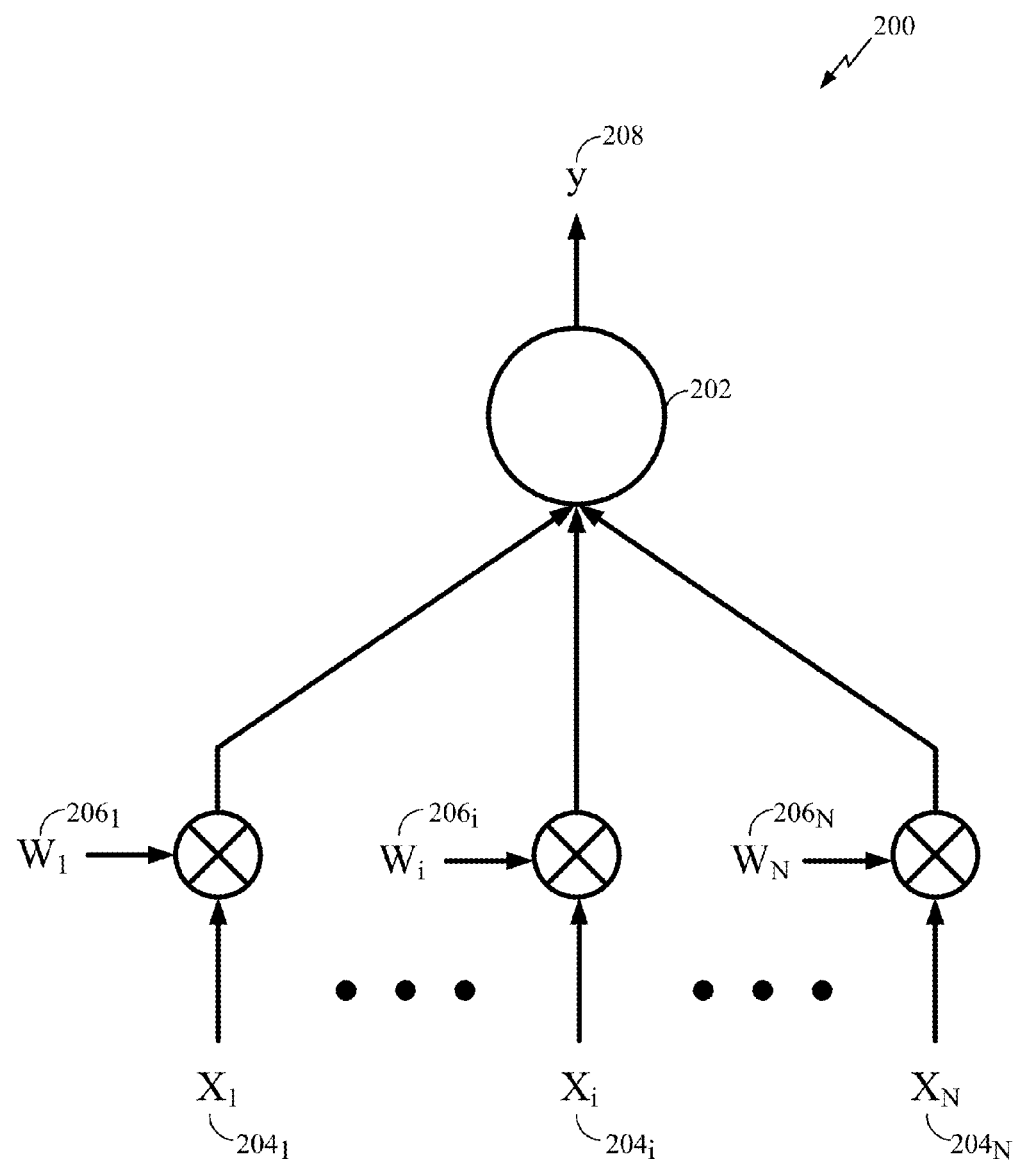
FIG. 2 illustrates an example of a processing unit (neuron) of a computational network (neural system or neural network) in accordance with certain aspects of the present disclosure.

FIG. 2 illustrates an exemplary diagram 200 of a processing unit (e.g., a neuron or neuron circuit) 202 of a computational network (e.g., a neural system or a neural network) in accordance with certain aspects of the present disclosure. For example, the neuron 202 may correspond to any of the neurons of levels 102 and 106 from FIG. 1. The neuron 202 may receive multiple input signals $204_1$-$204_N$, which may be signals external to the neural system, or signals generated by other neurons of the same neural system, or both. The input signal may be a current, a conductance, a voltage, a real-valued, and/or a complex-valued. The input signal may comprise a numerical value with a fixed-point or a floating-point representation. These input signals may be delivered to the neuron 202 through synaptic connections that scale the signals according to adjustable synaptic weights $206_1$-$206_N$ ($W_1$-$W_N$), where N may be a total number of input connections of the neuron 202.

The neuron 202 may combine the scaled input signals and use the combined scaled inputs to generate an output signal 208 (i.e., a signal Y). The output signal 208 may be a current, a conductance, a voltage, a real-valued and/or a complex-valued. The output signal may be a numerical value with a fixed-point or a floating-point representation. The output signal 208 may be then transferred as an input signal to other neurons of the same neural system, or as an input signal to the same neuron 202, or as an output of the neural system.

The processing unit (neuron) 202 may be emulated by an electrical circuit, and its input and output connections may be emulated by electrical connections with synaptic circuits. The processing unit 202 and its input and output connections may also be emulated by a software code. The processing unit 202 may also be emulated by an electric circuit, whereas its input and output connections may be emulated by a software code. In an aspect, the processing unit 202 in the computational network may be an analog electrical circuit. In another aspect, the processing unit 202 may be a digital electrical circuit. In yet another aspect, the processing unit 202 may be a mixed-signal electrical circuit with both analog and digital components. The computational network may include processing units in any of the aforementioned forms. The computational network (neural system or neural network) using such processing units may be utilized in a large range of applications, such as image and pattern recognition, machine learning, motor control, and the like.

During the course of training a neural network, synaptic weights (e.g., the weights $w_1^{(i,i+1)}$, ..., $w_P^{(i,i+1)}$ from FIG. 1 and/or the weights $206_1$-$206_N$ from FIG. 2) may be initialized with random values and increased or decreased according to a learning rule. Those skilled in the art will appreciate that examples of the learning rule include, but are not limited to the spike-timing-dependent plasticity (STDP) learning rule, the Hebb rule, the Oja rule, the Bienenstock-Copper-Munro (BCM) rule, etc. In certain aspects, the weights may settle or converge to one of two values (i.e., a bimodal distribution of weights). This effect can be utilized to reduce the number of bits for each synaptic weight, increase the speed of reading and writing from/to a memory storing the synaptic weights, and to reduce power and/or processor consumption of the synaptic memory.

Synapse Type

In hardware and software models of neural networks, the processing of synapse related functions can be based on synaptic type. Synapse types may be non-plastic synapses (no changes of weight and delay), plastic synapses (weight may change), structural delay plastic synapses (weight and delay may change), fully plastic synapses (weight, delay and connectivity may change), and variations thereupon (e.g., delay may change, but no change in weight or connectivity). The advantage of multiple types is that processing can be subdivided. For example, non-plastic synapses may not require plasticity functions to be executed (or waiting for such functions to complete). Similarly, delay and weight plasticity may be subdivided into operations that may operate together or separately, in sequence or in parallel. Different types of synapses may have different lookup tables or formulas and parameters for each of the different plasticity types that apply. Thus, the methods would access the relevant tables, formulas, or parameters for the synapse's type.

There are further implications of the fact that spike-timing dependent structural plasticity may be executed independently of synaptic plasticity. Structural plasticity may be executed even if there is no change to weight magnitude (e.g., if the weight has reached a minimum or maximum value, or it is not changed due to some other reason) s structural plasticity (i.e., an amount of delay change) may be a direct function of pre-post spike time difference. Alternatively, structural plasticity may be set as a function of the weight change amount or based on conditions relating to bounds of the weights or weight changes. For example, a synapse delay may change only when a weight change occurs or if weights reach zero but not if they are at a maximum value. However, it may be advantageous to have independent functions so that these processes can be parallelized reducing the number and overlap of memory accesses.

Determination of Synaptic Plasticity

Neuroplasticity (or simply "plasticity") is the capacity of neurons and neural networks in the brain to change their synaptic connections and behavior in response to new information, sensory stimulation, development, damage, or dysfunction. Plasticity is important to learning and memory in biology, as well as for computational neuroscience and neural networks. Various forms of plasticity have been studied, such as synaptic plasticity (e.g., according to the Hebbian theory), spike-timing-dependent plasticity (STDP), non-synaptic plasticity, activity-dependent plasticity, structural plasticity and homeostatic plasticity.

STDP is a learning process that adjusts the strength of synaptic connections between neurons. The connection strengths are adjusted based on the relative timing of a particular neuron's output and received input spikes (i.e., action potentials). Under the STDP process, long-term potentiation (LTP) may occur if an input spike to a certain neuron tends, on average, to occur immediately before that neuron's output spike. Then, that particular input is made somewhat stronger. On the other hand, long-term depression (LTD) may occur if an input spike tends, on average, to occur immediately after an output spike. Then, that particular input is made somewhat weaker, and hence the name "spike-timing-dependent plasticity." Consequently, inputs that might be the cause of the postsynaptic neuron's excitation are made even more likely to contribute in the future, whereas inputs that are not the cause of the postsynaptic spike are made less likely to contribute in the future. The process continues until a subset of the initial set of connections remains, while the influence of all others is reduced to an insignificant level.

Because a neuron generally produces an output spike when many of its inputs occur within a brief period (i.e., being cumulative sufficient to cause the output), the subset of inputs that typically remains includes those that tended to be correlated in time. In addition, because the inputs that occur before the output spike are strengthened, the inputs that provide the earliest sufficiently cumulative indication of correlation will eventually become the final input to the neuron.

The STDP learning rule may effectively adapt a synaptic weight of a synapse connecting a presynaptic neuron to a postsynaptic neuron as a function of time difference between spike time $t_{pre}$ of the presynaptic neuron and spike time $t_{post}$ of the postsynaptic neuron (i.e., $t=t_{post}-t_{pre}$). A typical formulation of the STDP is to increase the synaptic weight (i.e., potentiate the synapse) if the time difference is positive (the presynaptic neuron fires before the postsynaptic neuron), and decrease the synaptic weight (i.e., depress the synapse) if the time difference is negative (the postsynaptic neuron fires before the presynaptic neuron).

In the STDP process, a change of the synaptic weight over time may be typically achieved using an exponential decay, as given by:

$$\Delta w(t) = \begin{cases} a_+ e^{-t/k_+} + \mu, & t > 0 \\ a_- e^{t/k_-}, & t < 0 \end{cases} \quad (1)$$

where $k_+$ and $k_{-sign(\Delta t)}$ are time constants for positive and negative time difference, respectively, $a_+$ and $a_-$ are corresponding scaling magnitudes, and $\mu$ is an offset that may be applied to the positive time difference and/or the negative time difference.

Figure 3:
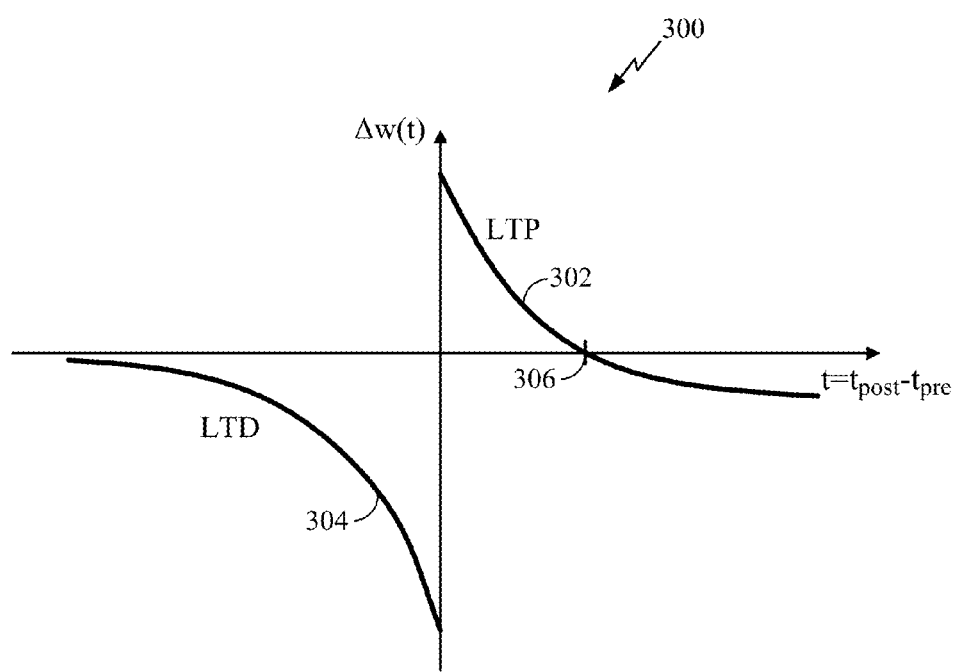
FIG. 3 illustrates an example of spike-timing dependent plasticity (STDP) curve in accordance with certain aspects of the present disclosure.

FIG. 3 illustrates an exemplary diagram 300 of a synaptic weight change as a function of relative timing of presynaptic and postsynaptic spikes in accordance with the STDP. If a presynaptic neuron fires before a postsynaptic neuron, then a corresponding synaptic weight may be increased, as illustrated in a portion 302 of the graph 300. This weight increase can be referred to as an LTP of the synapse. It can be observed from the graph portion 302 that the amount of LTP may decrease roughly exponentially as a function of the difference between presynaptic and postsynaptic spike times. The reverse order of firing may reduce the synaptic weight, as illustrated in a portion 304 of the graph 300, causing an LTD of the synapse.

As illustrated in the graph 300 in FIG. 3, a negative offset $\mu$ may be applied to the LTP (causal) portion 302 of the STDP graph. A point of cross-over 306 of the x-axis (y=0) may be configured to coincide with the maximum time lag for considering correlation for causal inputs from layer i−1. In the case of a frame-based input (i.e., an input that is in the form of a frame of a particular duration comprising spikes or pulses), the offset value $\mu$ can be computed to reflect the frame boundary. A first input spike (pulse) in the frame may be considered to decay over time either as modeled by a postsynaptic potential directly or in terms of the effect on neural state. If a second input spike (pulse) in the frame is considered correlated or relevant to a particular time frame, then the relevant times before and after the frame may be separated at that time frame boundary and treated differently in plasticity terms by offsetting one or more parts of the STDP curve such that the value in the relevant times may be different (e.g., negative for greater than one frame and positive for less than one frame). For example, the negative offset $\mu$ may be set to offset LTP such that the curve actually goes below zero at a pre-post time greater than the frame time and it is thus part of LTD instead of LTP.

Neuron Models and Operation

There are some general principles for designing a useful spiking neuron model. A good neuron model may have rich potential behavior in terms of two computational regimes: coincidence detection and functional computation. Moreover, a good neuron model should have two elements to allow temporal coding: arrival time of inputs affects output time and coincidence detection can have a narrow time window. Finally, to be computationally attractive, a good neuron model may have a closed-form solution in continuous time and stable behavior including near attractors and saddle points. In other words, a useful neuron model is one that is practical and that can be used to model rich, realistic and biologically-consistent behaviors, as well as be used to both engineer and reverse engineer neural circuits.

A neuron model may depend on events, such as an input arrival, output spike or other event whether internal or external. To achieve a rich behavioral repertoire, a state machine that can exhibit complex behaviors may be desired. If the occurrence of an event itself, separate from the input contribution (if any), can influence the state machine and constrain dynamics subsequent to the event, then the future state of the system is not only a function of a state and input, but rather a function of a state, event, and input.

In an aspect, a neuron n may be modeled as a spiking leaky-integrate-and-fire neuron with a membrane voltage $v_n(t)$ governed by the following dynamics:

$$\frac{dv_n(t)}{dt} = \alpha v_n(t) + \beta \sum_m w_{m,n} y_m(t - \Delta t_{m,n}), \quad (2)$$

where α and β are parameters, $w_{m,n}$ is a synaptic weight for the synapse connecting a presynaptic neuron m to a postsynaptic neuron n, and $y_m(t)$ is the spiking output of the neuron m that may be delayed by dendritic or axonal delay according to $\Delta t_{m,n}$ until arrival at the neuron n's soma.

It should be noted that there is a delay from the time when sufficient input to a postsynaptic neuron is established until the time when the postsynaptic neuron actually fires. In a dynamic spiking neuron model, such as Izhikevich's simple model, a time delay may be incurred if there is a difference between a depolarization threshold $v_t$ and a peak spike voltage $v_{peak}$. For example, in the simple model, neuron soma dynamics can be governed by the pair of differential equations for voltage and recovery, i.e.:

$$\frac{dv}{dt} = (k(v - v_t)(v - v_r) - u + I)/C, \quad (3)$$

$$\frac{du}{dt} = a(b(v - v_r) - u). \quad (4)$$

where v is a membrane potential, u is a membrane recovery variable, k is a parameter that describes time scale of the membrane potential v, a is a parameter that describes time scale of the recovery variable u, b is a parameter that describes sensitivity of the recovery variable u to the sub-threshold fluctuations of the membrane potential v, $v_r$ is a membrane resting potential, I is a synaptic current, and C is a membrane's capacitance. In accordance with this model, the neuron is defined to spike when $v > v_{peak}$.

Hunzinger Cold Model

The Hunzinger Cold neuron model is a minimal dual-regime spiking linear dynamical model that can reproduce a rich variety of neural behaviors. The model's one- or two-dimensional linear dynamics can have two regimes, wherein the time constant (and coupling) can depend on the regime. In the sub-threshold regime, the time constant, negative by convention, represents leaky channel dynamics generally acting to return a cell to rest in a biologically-consistent linear fashion. The time constant in the supra-threshold regime, positive by convention, reflects anti-leaky channel dynamics generally driving a cell to spike while incurring latency in spike-generation.

Figure 4:
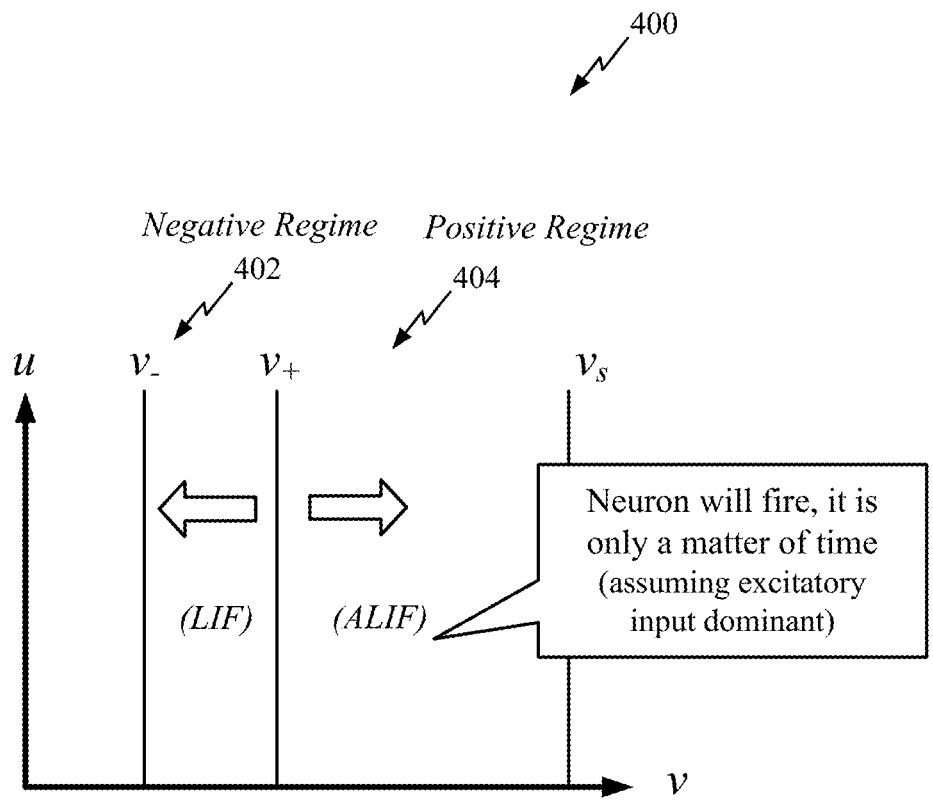
FIG. 4 illustrates an example of a positive regime and a negative regime for defining behavior of a neuron model in accordance with certain aspects of the present disclosure.

As illustrated in FIG. 4, the dynamics of the model 400 may be divided into two (or more) regimes. These regimes may be called the negative regime 402 (also interchangeably referred to as the leaky-integrate-and-fire (LIF) regime, not to be confused with the LIF neuron model) and the positive regime 404 (also interchangeably referred to as the anti-leaky-integrate-and-fire (ALIF) regime, not to be confused with the ALIF neuron model). In the negative regime 402, the state tends toward rest ($v_-$) at the time of a future event. In this negative regime, the model generally exhibits temporal input detection properties and other sub-threshold behavior. In the positive regime 404, the state tends toward a spiking event ($v_s$). In this positive regime, the model exhibits computational properties, such as incurring a latency to spike depending on subsequent input events. Formulation of dynamics in terms of events and separation of the dynamics into these two regimes are fundamental characteristics of the model.

Linear dual-regime bi-dimensional dynamics (for states v and u) may be defined by convention as:

$$\tau_\rho \frac{dv}{dt} = v + q_\rho \quad (5)$$

$$-\tau_u \frac{du}{dt} = u + r \quad (6)$$

where $q_\rho$ and r are the linear transformation variables for coupling.

The symbol ρ is used herein to denote the dynamics regime with the convention to replace the symbol ρ with the sign "−" or "+" for the negative and positive regimes, respectively, when discussing or expressing a relation for a specific regime.

The model state is defined by a membrane potential (voltage) v and recovery current u. In basic form, the regime is essentially determined by the model state. There are subtle, but important aspects of the precise and general definition, but for the moment, consider the model to be in the positive regime 404 if the voltage v is above a threshold ($v_+$) and otherwise in the negative regime 402.

The regime-dependent time constants include $\tau_-$ which is the negative regime time constant, and $\tau_+$ which is the positive regime time constant. The recovery current time constants $\tau_u$ is typically independent of regime. For convenience, the negative regime time constant $\tau_-$ is typically specified as a negative quantity to reflect decay so that the same expression for voltage evolution may be used as for the positive regime in which the exponent and $\tau_+$ will generally be positive, as will be $\tau_u$.

The dynamics of the two state elements may be coupled at events by transformations offsetting the states from their null-clines, where the transformation variables are:

$$q_\rho = -\tau_\rho \beta u - v_\rho \quad (7)$$

$$r = \delta(v + \epsilon) \quad (8)$$

where δ, ε, β and $v_-$, $v_+$ are parameters. The two values for $v_\rho$ are the base for reference voltages for the two regimes. The parameter $v_-$ is the base voltage for the negative regime, and the membrane potential will generally decay toward $v_-$ in the negative regime. The parameter $v_+$ is the base voltage for the positive regime, and the membrane potential will generally tend away from $v_+$ in the positive regime.

The null-clines for v and u are given by the negative of the transformation variables $q_\rho$ and r, respectively. The parameter δ is a scale factor controlling the slope of the u null-cline. The parameter ε is typically set equal to $-v_-$. The parameter β is a resistance value controlling the slope of the v null-clines in both regimes. The $\tau_\rho$ time-constant parameters control not only the exponential decays, but also the null-cline slopes in each regime separately.

The model may be defined to spike when the voltage v reaches a value $v_S$. Subsequently, the state may be reset at a reset event (which may be one and the same as the spike event):

$$v = \hat{v}_- \quad (9)$$

$$u = u + \Delta u \quad (10)$$

where $\hat{v}_-$ and $\Delta u$ are parameters. The reset voltage $\hat{v}_-$ is typically set to $v_-$.

By a principle of momentary coupling, a closed form solution is possible not only for state (and with a single exponential term), but also for the time required to reach a particular state. The close form state solutions are:

$$v(t + \Delta t) = (v(t) + q_\rho)e^{\frac{\Delta t}{\tau_\rho}} - q_\rho \quad (11)$$

$$u(t + \Delta t) = (u(t) + r)e^{-\frac{\Delta t}{\tau_u}} - r \quad (12)$$

Therefore, the model state may be updated only upon events, such as an input (presynaptic spike) or output (postsynaptic spike). Operations may also be performed at any particular time (whether or not there is input or output).

Moreover, by the momentary coupling principle, the time of a postsynaptic spike may be anticipated so the time to reach a particular state may be determined in advance without iterative techniques or Numerical Methods (e.g., the Euler numerical method). Given a prior voltage state $v_0$, the time delay until voltage state $v_f$ is reached is given by:

$$\Delta t = \tau_\rho \log \frac{v_f + q_\rho}{v_0 + q_\rho} \quad (13)$$

If a spike is defined as occurring at the time the voltage state v reaches $v_S$, then the closed-form solution for the amount of time, or relative delay, until a spike occurs as measured from the time that the voltage is at a given state v is:

$$\Delta t_S = \begin{cases} \tau_+ \log \frac{v_S + q_+}{v + q_+} & \text{if } v > \hat{v}_+ \\ \infty & \text{otherwise} \end{cases} \quad (14)$$

where $\hat{v}_+$ is typically set to parameter $v_+$, although other variations may be possible.

The above definitions of the model dynamics depend on whether the model is in the positive or negative regime. As mentioned, the coupling and the regime ρ may be computed upon events. For purposes of state propagation, the regime and coupling (transformation) variables may be defined based on the state at the time of the last (prior) event. For purposes of subsequently anticipating spike output time, the regime and coupling variable may be defined based on the state at the time of the next (current) event.

There are several possible implementations of the Cold model, and executing the simulation, emulation or model in time. This includes, for example, event-update, step-event update, and step-update modes. An event update is an update where states are updated based on events or "event update" (at particular moments). A step update is an update when the model is updated at intervals (e.g., 1 ms). This does not necessarily require iterative methods or Numerical methods. An event-based implementation is also possible at a limited time resolution in a step-based simulator by only updating the model if an event occurs at or between steps or by "step-event" update.

Phase-Coding for Coordinate Transformation

Objects, such as robots or autonomous devices, may be specified to select a target in an environment. The position of the target specified for the object may be based on a world view, such as a view based on the user's position. Still, to improve performance, it is desirable to transform the coordinates of the target(s) to be relative to the object's position.

Coordinate transformation may refer to the conversion of a representation of space relative to a first reference frame to a substantially similar representation relative to a second reference frame. For example, an object, such as a robot, may be given a set of coordinates for a target relative to the northwest corner of a room. In this example, the coordinates for the target are based on a world-centric reference frame (i.e., allocentric coordinate representation). Still, for a robot to plan a movement toward that target, it is desirable to convert the allocentric coordinates to a representation relative to the robot's current position and direction (i.e., egocentric reference frame).

Specifically, for a robot to plan a movement toward that target, the allocentric coordinates should be converted to egocentric coordinates. The egocentric coordinates of the target would change as the robot moved around the room, still, the allocentric coordinates would remain the same as the robot moved around the room. It would be desirable to maintain the egocentric coordinates based on a fixed position for the robot, such as a center of a map.

Aspects of the present disclosure are directed to converting allocentric coordinates to egocentric coordinates based on adjusting a spiking phase of a neuron. In neuroscience, coordinate transformations are performed by gain fields within spiking networks. Gain fields specify a representation of space that is different from the implemented representation. Additionally, gain fields provide for multiplicative interactions between multiple synaptic inputs.

Figure 5A:
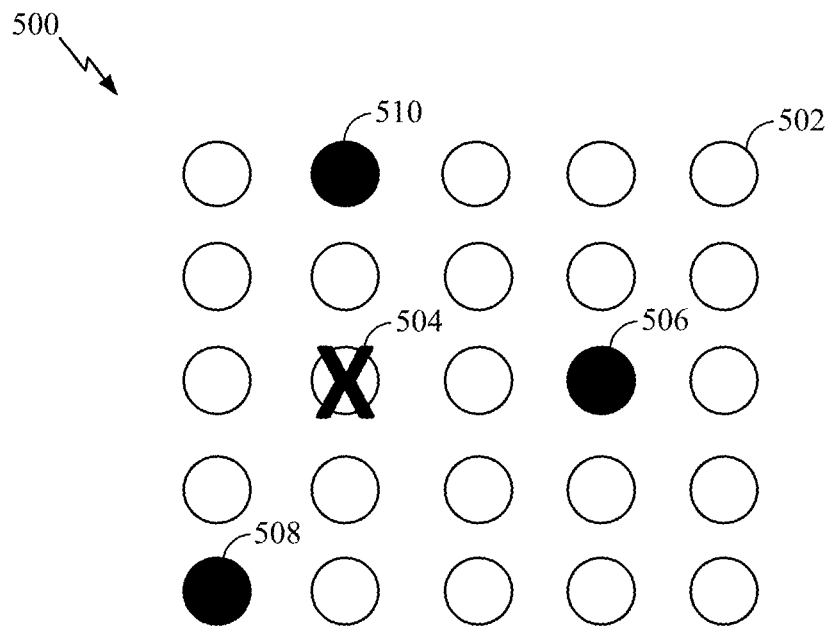
FIGS. 5A-5B illustrate examples of transforming coordinates according to an aspect of the present disclosure.
Figure 5B:
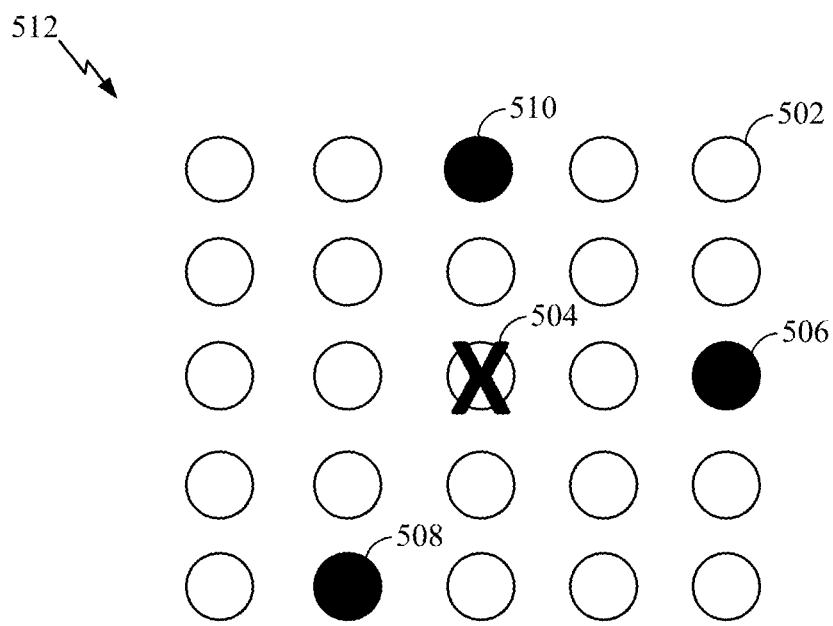

FIGS. 5A-5B illustrate examples of a conversion of allocentric coordinates to egocentric coordinates. The maps of FIG. 5A-5B are based on 2-dimensional (2D) representations of a space that includes targets and an object, such as a robot. That is, both an allocentric space and an egocentric space may be represented by a 2D grid of cells. Each cell represents a location in real space and the activity, such as the spiking activity, of the cell may represent an attribute about that location, such as the presence or absence of a target.

In one configuration, the transformation of an allocentric representation to an egocentric representation is performed by mapping targets represented in a 2D grid from an allocentric representation to an egocentric representation. The robot may be centered in the map for the egocentric representation. The transformation uses the current position of the object in allocentric coordinates. The current position of the object is represented by a grid of place cells. A place cell map of the only the object may be specified. That is, a place cell map comprising a grid of cells may be specified and the location of the object may be specified based on the activity of a cell.

FIG. 5A illustrates an allocentric map 500 of an object 504 and targets 506, 508, 510. The allocentric map 500 is represented by a grid of place cells 502. As shown in FIG. 5A, the location of the object 504 is not in the center of the map 500. That is, the coordinates for the object 504 and the targets 506, 508, 510 are based on a world-centric reference frame. In one configuration, the allocentric map 500 shown in FIG. 5A may be converted to an egocentric map 512 shown in FIG. 5B. Specifically, as shown in FIG. 5B, the location of the object 504 is in the center of the map 512. That is, in contrast to the allocentric map 500 (FIG. 5A), the coordinates for the object 504 and the targets 506, 508, 510 in the egocentric map 512 (FIG. 5B) are based on a reference frame from the object's position.

As previously discussed, the allocentric map 500 may be represented by a 2D grid of cells. The presence of a target at a location may be indicated by the spiking interval of a cell. In one configuration, a map of target cells is converted to a phase-coded representation that represents position using a spiking phase. That is, the map of target cells may be represented by a grid representation and/or a phase-coded representation.

Figure 6:
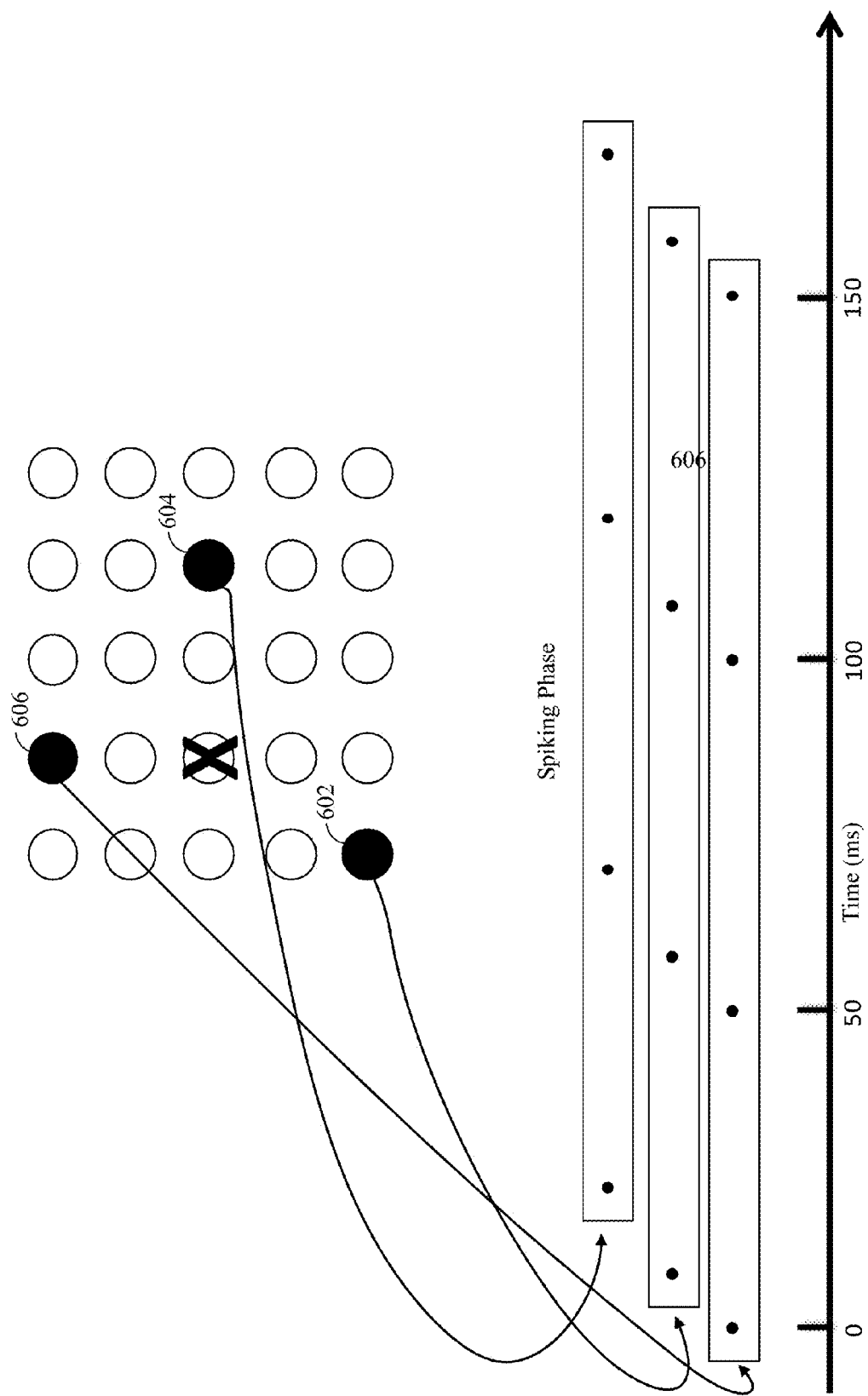
FIG. 6 illustrates a grid representation and phase-coded representation of target cells according to an aspect of the present disclosure.

FIG. 6 illustrates the spiking phase of each target cell according to an aspect of the present disclosure. Specifically, as shown in FIG. 6, each target cell may spike with a specific periodicity. Thus, because each cell may have a periodic spiking pattern, the phase of the spiking rate of the cells may be compared to each other. In one example, a first target cell 602 spikes once every 50 ms. Specifically, in this example, the first target cell spikes at times 0, 50, 100, 150, etc. Additionally, the spiking phase of the first target cell is different from the spiking phase of the other target cells 604, 606. That is, as shown in FIG. 6 each cell may spike at the same frequency, such as once every 50 ms, still, the cells may spike at different phases (i.e., times).

Thus, in addition to representing the targets spatially in a 2D grid, the targets may also be represented as phases. Moreover, the offset of the phases may represent the position of the target cell in the grid. That is, in one configuration, each target cell is associated with a specific phase (0 . . . n) that represents the position of the target cell in the grid. In the present configuration, the first target 602 is in the first position in the grid of cells and has a phase of zero. Additionally, the second target 604 is in the fourteenth position and has a phase of thirteen. Finally, the third target 606 is in the twenty-second position and has a phase of twenty-one.

The physical position of a cell within a grid is generally accepted as being fixed, but the phase of the spiking of an active cell may be modified by other synaptic input. In one configuration, the place cell input may modify the phase of the active cells in the phase-coded representation to mimic the phase of the desired output position. In the present configuration, the place cell input may be wired to the phase-coded cells such that the phase of the cells in the phase-coded representation is shifted appropriately given the active place cell. The phase may be forward shifted (i.e., decreasing the phase) via excitatory connections. Moreover, the phase may be delayed (i.e., increasing the phase) via inhibitory connections.

Figure 7:
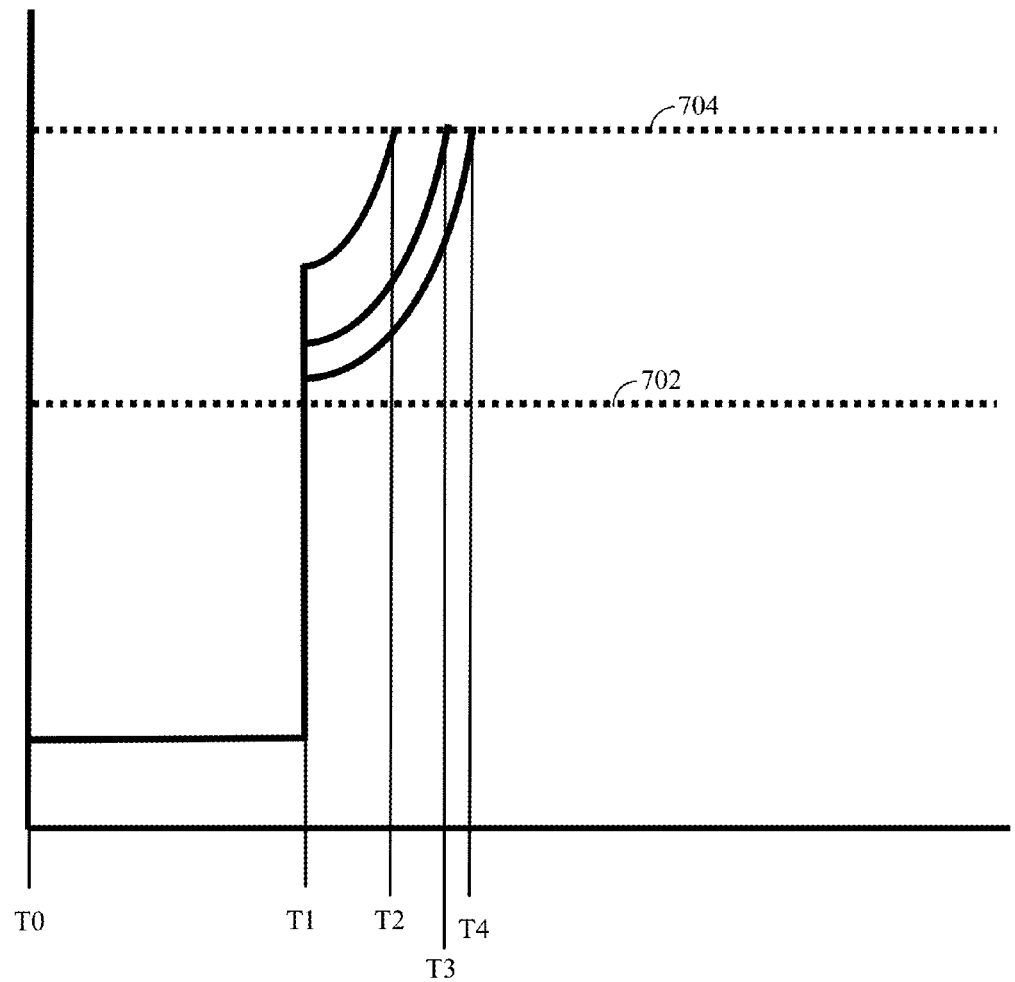
FIG. 7 illustrates an example of adjusting the spiking phase of a cell according to an aspect of the present disclosure.

FIG. 7 illustrates an example of adjusting the spiking phase of a cell according to an aspect of the present disclosure. As shown in FIG. 7, the x-axis represents time and the y-axis represents a membrane potential. In one configuration, as shown in FIG. 7, at time T0 a cell is at a resting potential. At time T1, the cell receives an input that triggers a response. Typically, the potential decays back to the resting potential if it is not greater than an anti-leaky integrate and fire (ALIF) threshold 702. Alternatively, if the potential is greater than the anti-leaky integrate and fire threshold 702, the potential decays upward to a spike threshold 704. The potential is considered a spike when the potential is greater than the spiking threshold.

Accordingly, because the membrane potential has an upward decay when it is greater than the ALIF threshold, the upward decay may be forward shifted or delayed. That is, in one configuration, an excitatory input may be applied to the input received at time T1 so that the membrane potential is increased to be closer to the spiking threshold. As shown in FIG. 7, the excitatory input may be input at so that the membrane potential may spike at a time T2. Alternatively, inhibitory inputs may be applied to the input received at time T1 so that the spiking is delayed. For example, as shown in FIG. 7, the membrane potential may be delayed to spike at time T3 or time T4. Thus, the spike timing of a cell may be adjusted based on an excitatory input or inhibitory input applied to the cell. The inhibitory input and excitatory inputs may be provided at different times during the upward decay to modify the spiking of the potential as desired.

FIGS. 8A-8D illustrate examples of adjusting the phase-code of target cells to convert an allocentric map to an egocentric map according to an aspect of the present disclosure.

Figure 8A:
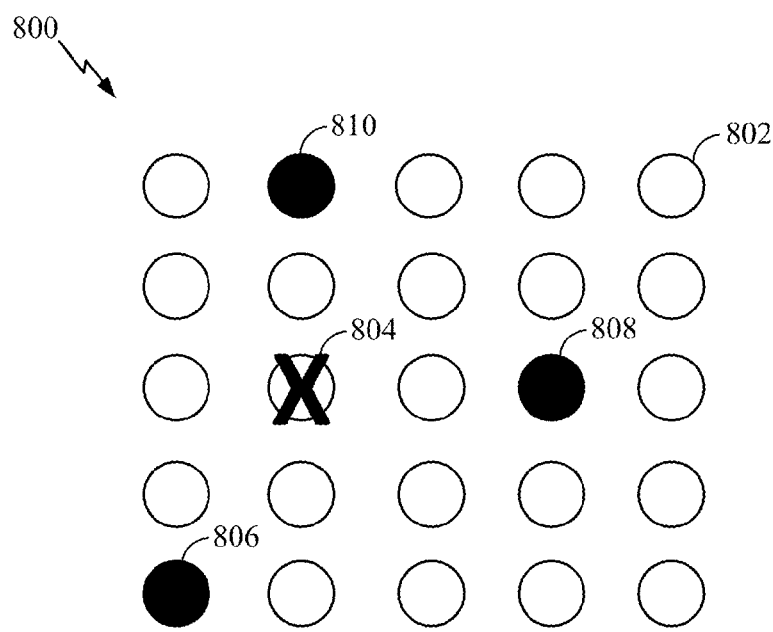
FIGS. 8A-8D illustrate examples of transforming coordinates according to an aspect of the present disclosure.

FIG. 8A illustrates a grid 800 of place cells 802 having an object 804 and targets 806, 808, 810. The grid 800 of FIG. 8A is based on an allocentric map, such that the location of the object 804 is not in the center of the grid 800. Specifically, the coordinates for the object 804 and the targets 806, 808, 810 are based on a world-centric reference frame. In one configuration, the grid 800 may be converted to an egocentric map.

Figure 8B:
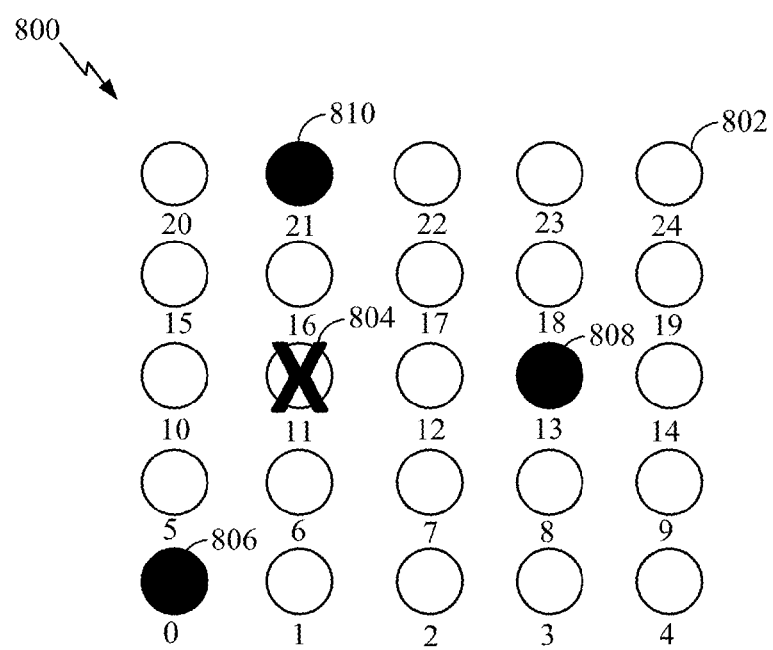

In the present configuration, the spiking phase of the targets 806, 808, 810 of the grid 800 are determined prior to the conversion. That is, a phase-coded allocentric map is generated based on the spiking phase of the target cells. As shown in FIG. 8B, the first target 806 has a spiking phase of zero, the second target 808 has a spiking phase of thirteen, and the third target 810 has a spiking phase of twenty-one. In the present example, the spiking phase of each target 806, 808, 810 is relative to the position (0 . . . n) in the grid of cells. That is, the first target 806 is at the first position in the grid of cells and has a phase of zero. Additionally, the second target 808 is in the fourteenth position and has a phase of thirteen. Finally, the third target 810 is in the twenty-second position and has a phase of twenty-one. FIG. 8B illustrates the network determining the spiking phase of each cell, still, in another configuration, the network only determines the spiking phase for target cells.

After determining the spiking phase of each target to generate a phase-coded allocentric map, such as the phase-coded allocentric map of FIG. 8B, the spiking phase of each target is perturbed so that the spiking phase is adjusted relative to the position of the object. That is, the spiking phase of each target is adjusted so that the targets are based on an egocentric map. The spiking phase of each target cell may be adjusted via an excitatory input or an inhibitory input. It should be noted that the system or user may be aware of the distance between the object and the center of the grid based on the place cell map of the object's position. Still, aspects of the current application are not limited to determining the object's position based on the place cell map of the object's position and other aspects for determining the object's position are also contemplated.

Figure 8C:
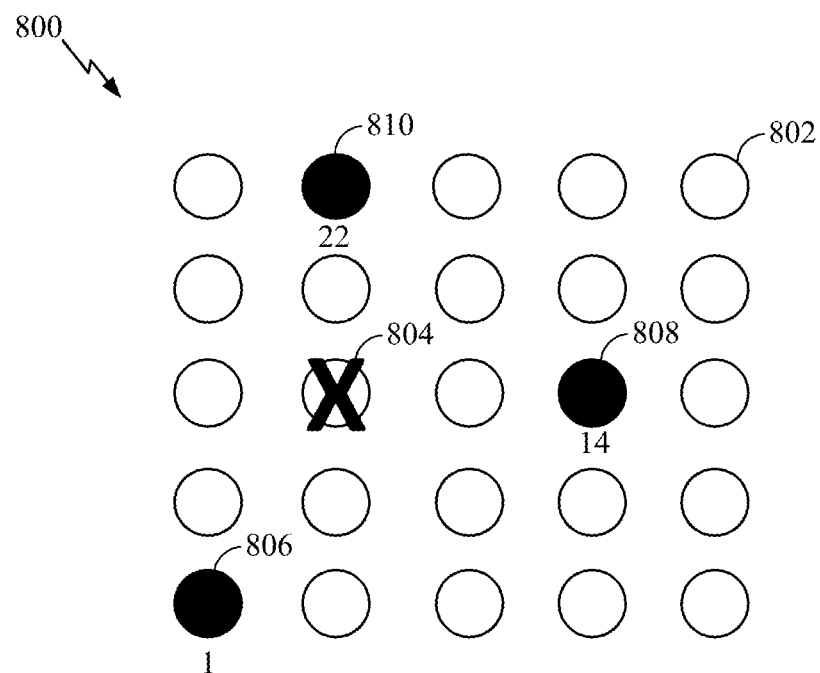

As previously discussed, an egocentric representation specifies that the object 804 be placed in the center of the grid 800. Accordingly, in the example shown in FIG. 8C, the object 804 is one cell away from the center of the grid. Thus, to convert the grid 800 to an egocentric map, a modified phase-coded map is generated. The modified phase-coded allocentric map adjusts the spiking phase of each target to compensate for the distance between the object and the center. The map of FIG. 8C is still an allocentric map because the object is still not centered, however, as shown in FIG. 8C, the spiking phase of each target 806, 808, 810 is adjusted to represent the spiking phase of the adjacent cell if the object 804 were in the center of the map. That is, the spiking phase of the first target 806 is adjusted from zero to one, the spiking phase of the second target 808 is adjusted from thirteen to fourteen, and the spiking phase of the third target 810 is adjusted from twenty-one to twenty-two.

Figure 8D:
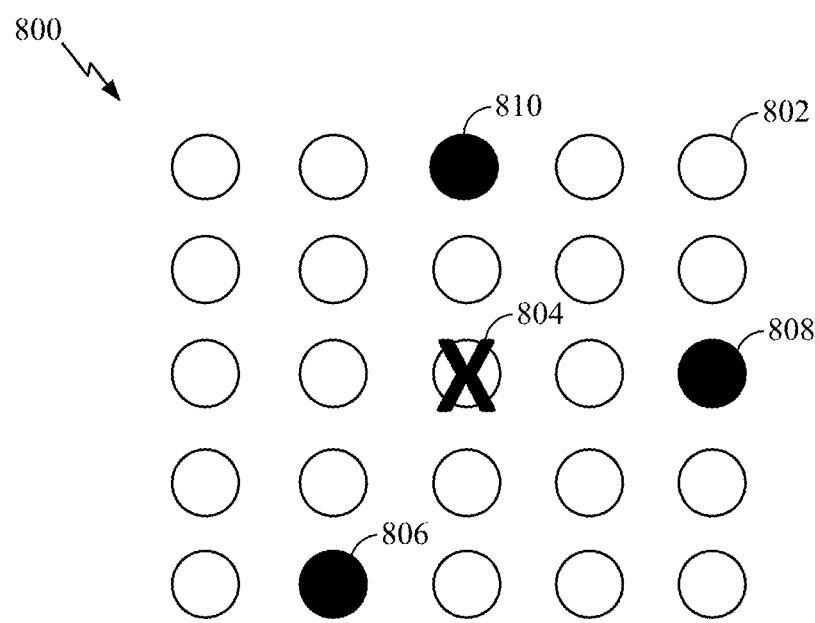

In the present configuration, based on the modified phase-coded allocentric map, an egocentric map may be generated. Specifically, the adjusted phases of the target cells are recovered to generate the egocentric map. As shown in FIG. 8D, the grid 800 is an egocentric map with the object 804 in the center of the grid 800. The egocentric map of FIG. 8D is based on the adjusted phases of the targets from the modified phase-coded allocentric map.

In one configuration, the phase-coded cells are specified to obtain the new position representation after the phase-coded cells have been modified by the place cell input. In the present configuration, to recover the transformed position, a second grid of cells is specified. The second grid of cells is tailored for the specific phases of spiking input at specific positions. The temporally tuned cells of the second grid are created by producing a set of cells spiking at all phases (i.e., phase cells) used in the network. Furthermore, the phase cells are combined with the outputs of the phase-coded cells. All of the phase-coded cells are connected to all of the output cells. An output cell will only spike when there is a spike coincidence between an input from a phase-coded cell and the output cell's specific phase cell.

In another configuration, specific positions within a matrix of cells may be wired from the target cell input to all possible shifts of that map. The place cell input selects, via inhibition, the shifted maps that are specified to perform the transformation.

In yet another configuration, the transformations may be stacked. That is, because phase is a relative quantity, an allocentric map may be transformed to a T0 map. Furthermore, the T0 map may be transformed to a T1 map as a relative offset from the T0 map. The stacking of transformations is not limited to two maps, as aspects of the present disclosure are also contemplated for one to n maps. In one configuration, the T0-Tn maps are egocentric maps.

Figure 9:
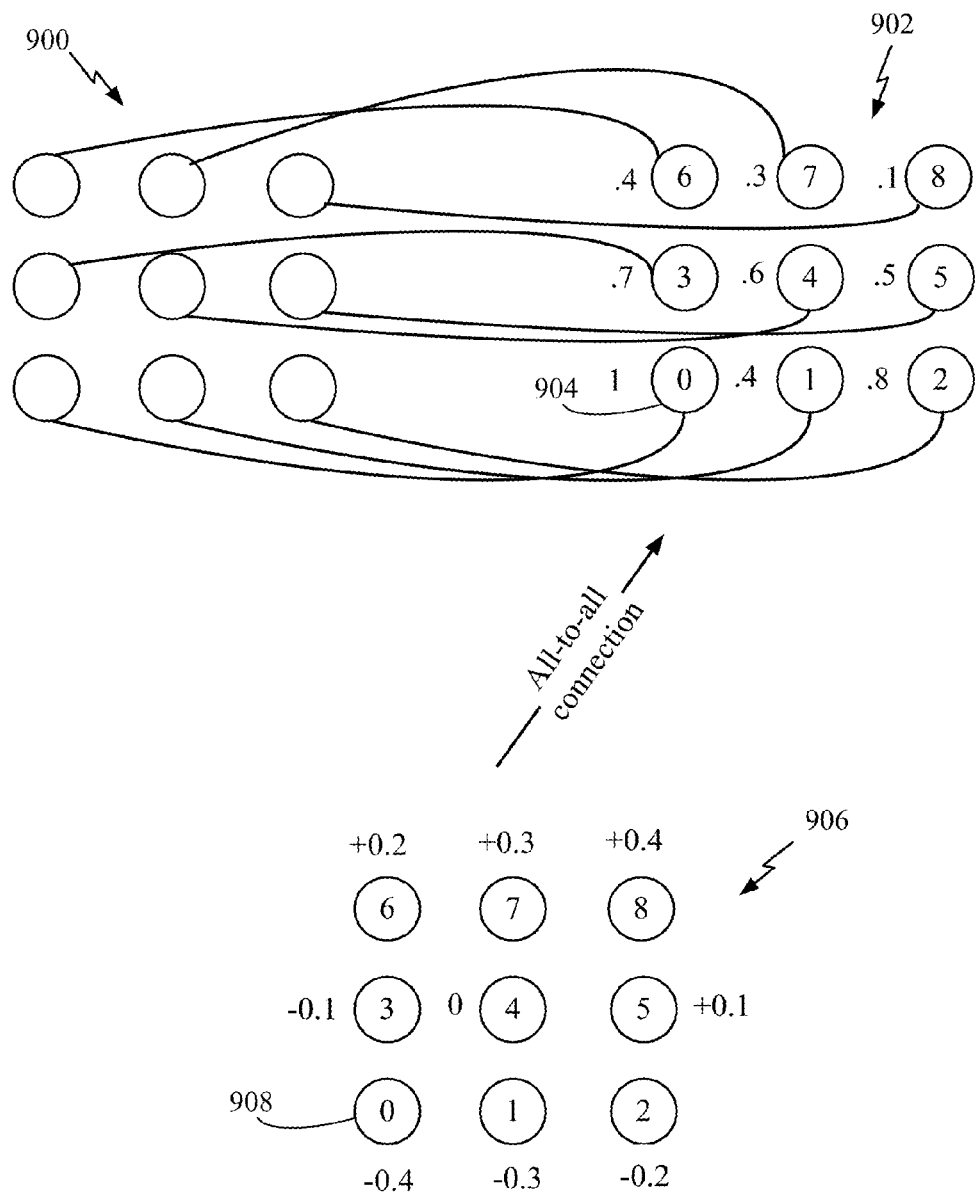
FIG. 9 illustrates the connection pattern from an allocentric map 900 to the phase-coded allocentric map 902 according to an aspect of the present disclosure

FIG. 9 illustrates a connection pattern from an allocentric map 900 to a phase-coded allocentric map 902 according to an aspect of the present disclosure. Specifically, as shown in FIG. 9, the allocentric map 900 has a one-to-one connection to the phase-coded allocentric map 902. Each cell of the phase-coded allocentric map 902 includes a weight and a phase. As an example, the first cell 904 of the phase-coded allocentric map 902 has a phase of zero and a weight of one.

The weights are specified so that the phase of the phase-coded map is representative of the position of the source cell. That is, zero is the phase for first cell 904 and eight is the phase of the last cell. Furthermore, the place cell map 906 has all-to-all connections (not-shown) to the phase-coded allocentric map 902. The connections of the all-to-all connections are specified so that the phase of the cells are shifted in a characteristic way that would put the active place cell into the center of the map. The active place cell is the position of the object, such as the robot, in world coordinates. As shown in FIG. 9, the weights of the place cell are adjusted so that the phase of the cells are shifted. For example, as shown in FIG. 9, the weight of a first cell 908 of the place cell map 906 is adjusted to −0.4.

Figure 10:
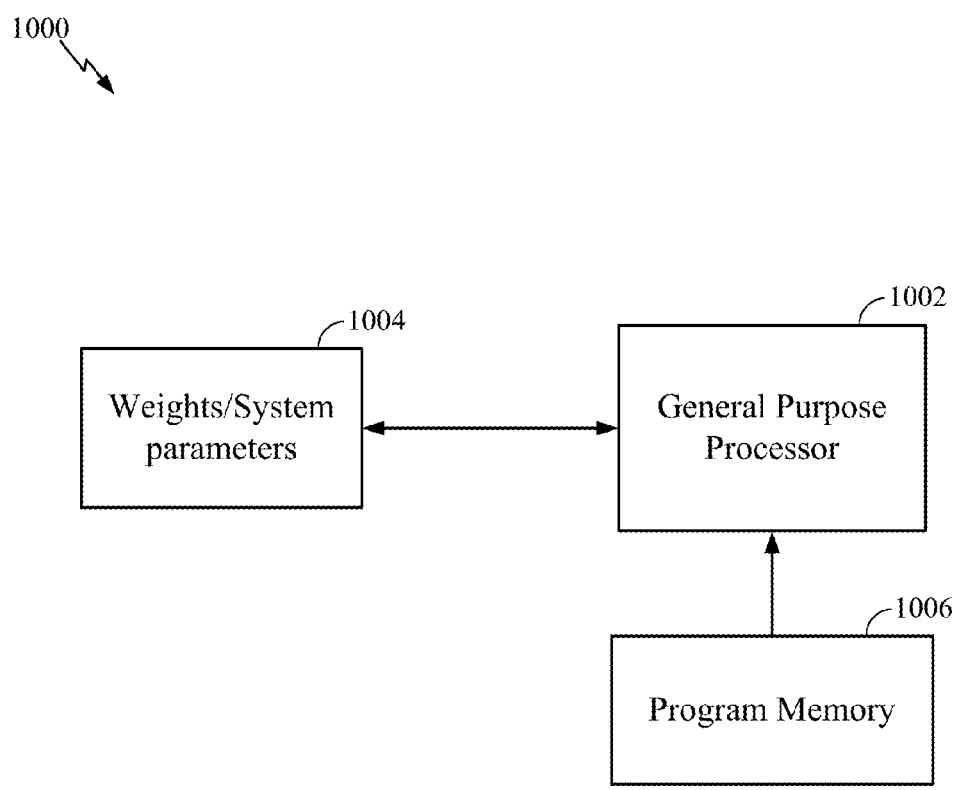
FIG. 10 illustrates an example implementation of designing a neural network using a general-purpose processor in accordance with certain aspects of the present disclosure.

FIG. 10 illustrates an example implementation 1000 of the aforementioned phase-coding transformation using a general-purpose processor 1002 in accordance with certain aspects of the present disclosure. Variables (neural signals), synaptic weights, system parameters associated with a computational network (neural network), delays, and frequency bin information may be stored in a memory block 1004, while instructions executed at the general-purpose processor 1002 may be loaded from a program memory 1006. In an aspect of the present disclosure, the instructions loaded into the general-purpose processor 1002 may comprise code for adjusting the phase-coding of target cells.

Figure 11:
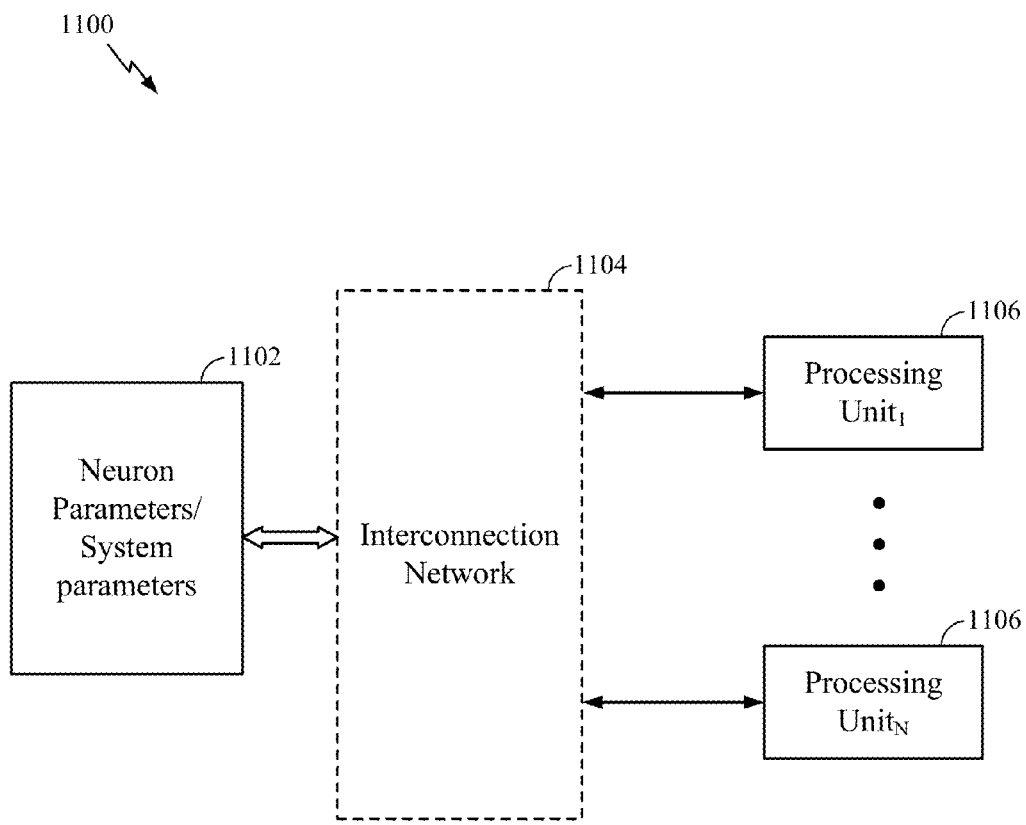
FIG. 11 illustrates an example implementation of designing a neural network where a memory may be interfaced with individual distributed processing units in accordance with certain aspects of the present disclosure.

FIG. 11 illustrates an example implementation 1100 of the aforementioned phase-coding transformation where a memory 1102 can be interfaced via an interconnection network 1104 with individual (distributed) processing units (neural processors) 1106 of a computational network (neural network) in accordance with certain aspects of the present disclosure. Variables (neural signals), synaptic weights, system parameters associated with the computational network (neural network) delays, frequency bin information, and spiking phases may be stored in the memory 1102, and may be loaded from the memory 1102 via connection(s) of the interconnection network 1104 into each processing unit (neural processor) 1106. In an aspect of the present disclosure, the processing unit 1106 may be configured to adjust the phase-coding of target cells.

Figure 12:
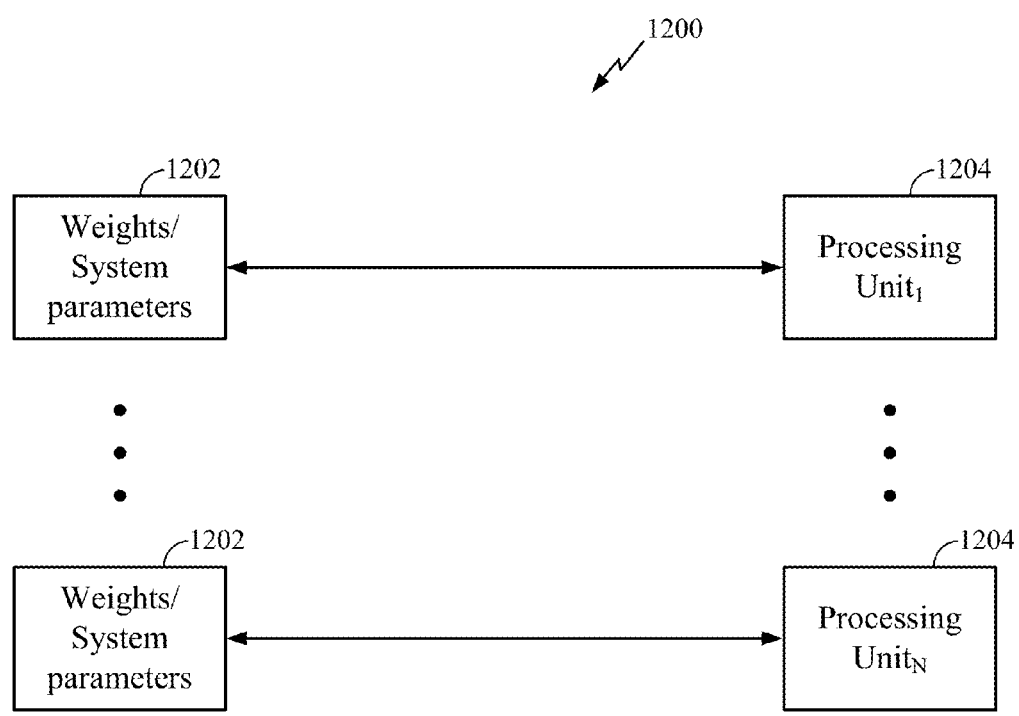
FIG. 12 illustrates an example implementation of designing a neural network based on distributed memories and distributed processing units in accordance with certain aspects of the present disclosure.

FIG. 12 illustrates an example implementation 1200 of the aforementioned phase-coding transformation. As illustrated in FIG. 12, one memory bank 1202 may be directly interfaced with one processing unit 1204 of a computational network (neural network). Each memory bank 1202 may store variables (neural signals), synaptic weights, and/or system parameters associated with a corresponding processing unit (neural processor) 1204 delays, frequency bin information, and spiking phases. In an aspect of the present disclosure, the processing unit 1204 may be configured to adjust the phase-coding of target cells.

Figure 13:
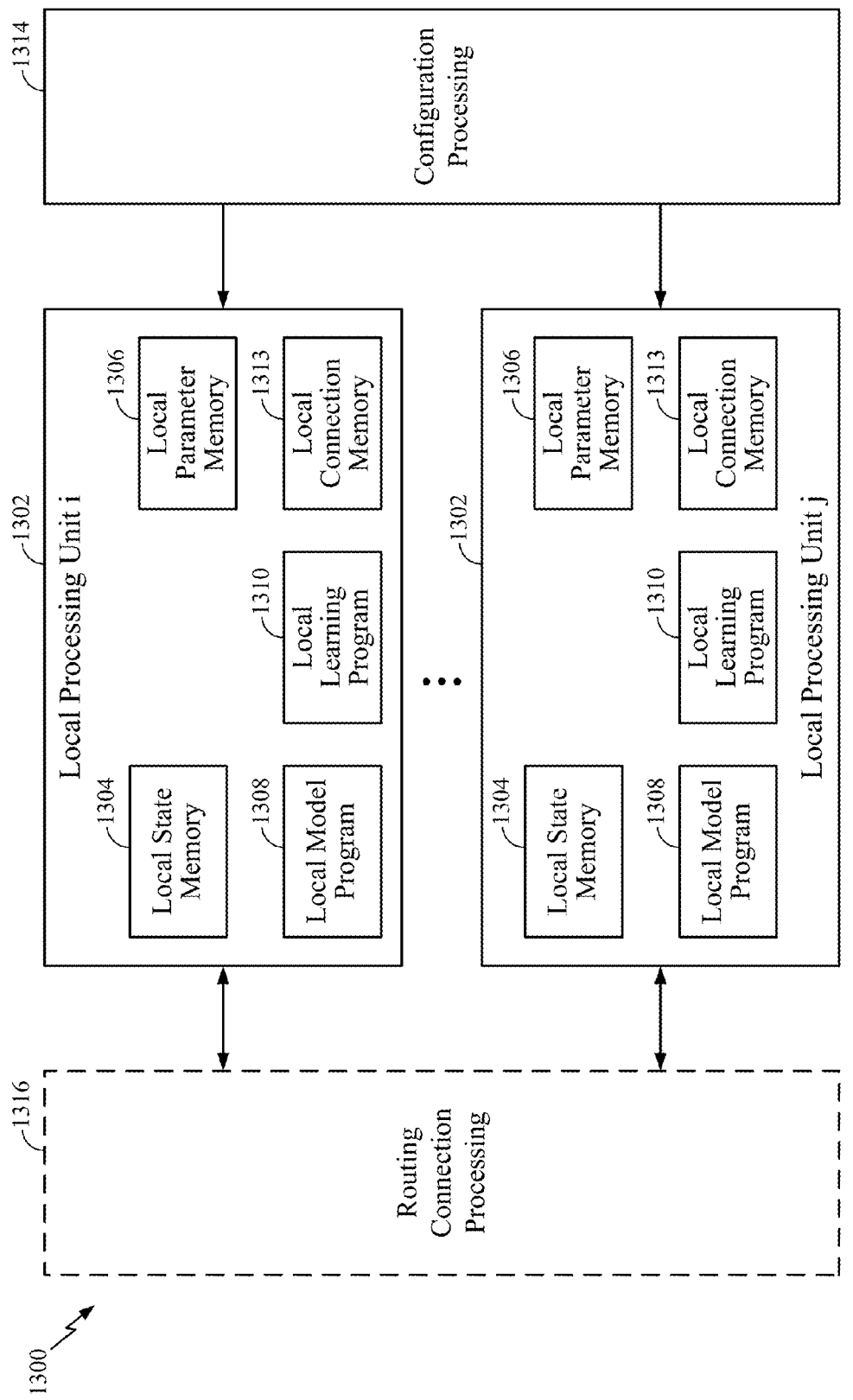
FIG. 13 illustrates an example implementation of a neural network in accordance with certain aspects of the present disclosure.

FIG. 13 illustrates an example implementation of a neural network 1300 in accordance with certain aspects of the present disclosure. As illustrated in FIG. 8, the neural network 1300 may have multiple local processing units 1302 that may perform various operations of methods described above. Each local processing unit 1302 may comprise a local state memory 1304 and a local parameter memory 1306 that store parameters of the neural network. In addition, the local processing unit 1302 may have a local (neuron) model program (LMP) memory 1308 for storing a local model program, a local learning program (LLP) memory 1310 for storing a local learning program, and a local connection memory 1313. Furthermore, as illustrated in FIG. 8, each local processing unit 1302 may be interfaced with a configuration processing unit 1314 for providing configurations for local memories of the local processing unit, and with a routing connection processing unit 1316 that provide routing between the local processing units 1302.

In one configuration, a neuron model is configured for obtaining prototypical neuron dynamics and/or modifying parameters of a neuron model. The neuron model includes an encoding means, and a shifting means. In one aspect, the encoding means, the shifting means may be the general-purpose processor 1002, program memory 1006, memory block 1004, memory 1102, interconnection network 1104, processing units 1106, processing unit 1204, local processing units 1302, and or the routing connection processing units 1316 configured to perform the functions recited. In another configuration, the aforementioned means may be any module or any apparatus configured to perform the functions recited by the aforementioned means.

According to certain aspects of the present disclosure, each local processing unit 1302 may be configured to determine parameters of the neural network based upon desired one or more functional features of the neural network, and develop the one or more functional features towards the desired functional features as the determined parameters are further adapted, tuned and updated.

Figure 14:
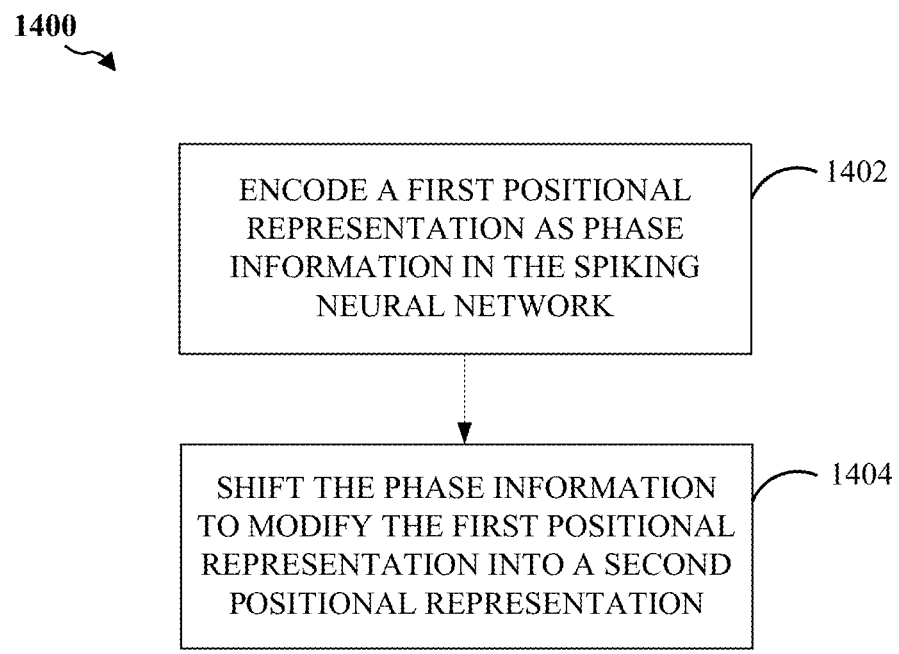
FIG. 14 is a block diagram illustrating coordinate transformation in accordance with an aspect of the present disclosure.

FIG. 14 illustrates a method 1400 of phase-coding for coordinate transformation. In block 1402, the neuron model encodes a first positional representation as phase information in the spiking neural network. Furthermore, in block 1404, the neuron model shifts the phase information to modify the first positional representation into a second positional representation.

The various operations of methods described above may be performed by any suitable means capable of performing the corresponding functions. The means may include various hardware and/or software component(s) and/or module(s), including, but not limited to, a circuit, an application specific integrated circuit (ASIC), or processor. Generally, where there are operations illustrated in the figures, those operations may have corresponding counterpart means-plus-function components with similar numbering.

As used herein, the term "determining" encompasses a wide variety of actions. For example, "determining" may include calculating, computing, processing, deriving, investigating, looking up (e.g., looking up in a table, a database or another data structure), ascertaining and the like. Additionally, "determining" may include receiving (e.g., receiving information), accessing (e.g., accessing data in a memory) and the like. Furthermore, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, erasable programmable read-only memory (EPROM), electrically erasable programmable read-only memory (EEPROM), registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in hardware, an example hardware configuration may comprise a processing system in a device. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement signal processing functions. For certain aspects, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processor may be responsible for managing the bus and general processing, including the execution of software stored on the machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, random access memory (RAM), flash memory, read only memory (ROM), programmable read-only memory (PROM), erasable programmable read-only memory (EPROM), electrically erasable programmable Read-only memory (EEPROM), registers, magnetic disks, optical disks, hard drives, or any other suitable storage medium, or any combination thereof. The machine-readable media may be embodied in a computer-program product. The computer-program product may comprise packaging materials.

In a hardware implementation, the machine-readable media may be part of the processing system separate from the processor. However, as those skilled in the art will readily appreciate, the machine-readable media, or any portion thereof, may be external to the processing system. By way of example, the machine-readable media may include a transmission line, a carrier wave modulated by data, and/or a computer product separate from the device, all which may be accessed by the processor through the bus interface. Alternatively, or in addition, the machine-readable media, or any portion thereof, may be integrated into the processor, such as the case may be with cache and/or general register files. Although the various components discussed may be described as having a specific location, such as a local component, they may also be configured in various ways, such as certain components being configured as part of a distributed computing system.

The processing system may be configured as a general-purpose processing system with one or more microprocessors providing the processor functionality and external memory providing at least a portion of the machine-readable media, all linked together with other supporting circuitry through an external bus architecture. Alternatively, the processing system may comprise one or more neuromorphic processors for implementing the neuron models and models of neural systems described herein. As another alternative, the processing system may be implemented with an application specific integrated circuit (ASIC) with the processor, the bus interface, the user interface, supporting circuitry, and at least a portion of the machine-readable media integrated into a single chip, or with one or more field programmable gate arrays (FPGAs), programmable logic devices (PLDs), controllers, state machines, gated logic, discrete hardware components, or any other suitable circuitry, or any combination of circuits that can perform the various functionality described throughout this disclosure. Those skilled in the art will recognize how best to implement the described functionality for the processing system depending on the particular application and the overall design constraints imposed on the overall system.

The machine-readable media may comprise a number of software modules. The software modules include instructions that, when executed by the processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module below, it will be understood that such functionality is implemented by the processor when executing instructions from that software module.

If implemented in software, the functions may be stored or transmitted over as one or more instructions or code on a computer-readable medium. Computer-readable media include both computer storage media and communication media including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. In addition, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A method for coordinate transformation in an artificial neural network, comprising:
    encoding a first positional representation as phase information of activities of cells of a first grid in the artificial neural network;
    determining a position of an object in relation to a center of the first grid, the position of the object corresponding to a non-centered cell of the first grid; and
    adjusting a weight of each cell of a second grid, which corresponds to the first grid, the weight adjusted to shift phase information of activity of each cell of the second grid to modify the first positional representation into a second positional representation, such that a position of the object in the second grid corresponds to a cell that is centered in the second grid.

2. The method of claim 1, in which the second positional representation is an egocentric representation.

3. The method of claim 1, in which the first positional representation is an allocentric representation.

4. The method of claim 1, in which the encoding comprises linearizing a plurality of coordinates corresponding to each cell of the first grid as a single set of phases.

5. The method of claim 4, in which the plurality of coordinates comprise polar coordinates.

6. The method of claim 1, in which the encoding comprises encoding a first coordinate as a first set of phases, and encoding a second coordinate as a second set of phases.

7. The method of claim 1, in which adjusting the weight excites or inhibits activity of each cell by an amount corresponding to a desired phase shift.

8. The method of claim 1, further comprising adjusting the adjusted weight of each cell to modify the second positional representation into a third positional representation.

9. An apparatus for coordinate transformation in an artificial neural network, comprising:
   a memory unit; and
   at least one processor coupled to the memory unit, the at least one processor being configured:
      to encode a first positional representation as phase information of activities of cells of a first grid in the-artificial neural network;
      to determine a position of an object in relation to a center of the first grid, the position of the object corresponding to a non-centered cell of the first grid; and
      to adjust a weight of each cell of a second grid, which corresponds to the first grid, the weight adjusted to shift phase information of activity of each cell of the second grid to modify the first positional representation into a second positional representation, such that a position of the object in the second grid corresponds to a cell that is centered in the second grid.

10. The apparatus of claim 9, in which the second positional representation is an egocentric representation.

11. The apparatus of claim 9, in which the first positional representation is an allocentric representation.

12. The apparatus of claim 9, in which the at least one processor is further configured to encode by linearizing a plurality of coordinates corresponding to each cell of the first grid as a single set of phases.

13. The apparatus of claim 12, in which the plurality of coordinates comprise polar coordinates.

14. The apparatus of claim 9, in which the at least one processor is further configured to encode a first coordinate as a first set of phases, and to encode a second coordinate as a second set of phases.

15. The apparatus of claim 9, in which the at least one processor is further configured to excite or inhibit activity of each cell by an amount corresponding to a desired phase shift based on the adjusted weight.

16. The apparatus of claim 9, in which the at least one processor is further configured to adjust the adjusted weight of each cell to modify the second positional representation into a third positional representation.

17. An apparatus for coordinate transformation in an artificial neural network, comprising:
   means for encoding a first positional representation as phase information of activities of cells of a first grid in the-artificial neural network;
   means for determining a position of an object in relation to a center of the first grid, the position of the object corresponding to a non-centered cell of the first grid; and
   means for adjusting a weight of each cell of a second grid, which corresponds to the first grid, the weight adjusted to shift phase information of activity of each cell of the second grid to modify the first positional representation into a second positional representation, such that a position of the object in the second grid corresponds to a cell that is centered in the second grid.

18. A non-transitory computer-readable medium having program code recorded thereon for coordinate transformation in an artificial neural network, the program code comprising:
   program code to encode a first positional representation as phase information of activities of cells of a first grid in the artificial neural network;
   program code to determine a position of an object in relation to a center of the first grid, the position of the object corresponding to a non-centered cell of the first grid; and
   program code to adjust a weight of each cell of a second grid, which corresponds to the first grid, the weight adjusted to shift phase information of activity of each cell of the second grid to modify the first positional representation into a second positional representation, such that a position of the object in the second grid corresponds to a cell that is centered in the second grid.

* * * * *